United States Patent
Kazemi Oskooei et al.

(10) Patent No.: US 11,942,189 B2
(45) Date of Patent: Mar. 26, 2024

(54) DRUG EFFICACY PREDICTION FOR TREATMENT OF GENETIC DISEASE

(71) Applicant: International Business Machines Corporation, Armonk, NY (US)

(72) Inventors: Seyed Ali Kazemi Oskooei, Zurich (CH); Maria Rodriguez Martinez, Thalwil (CH); Matteo Manica, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 1213 days.

(21) Appl. No.: 16/249,110

(22) Filed: Jan. 16, 2019

(65) Prior Publication Data

US 2020/0227134 A1 Jul. 16, 2020

(51) Int. Cl.
*G16H 50/50* (2018.01)
*G06N 20/00* (2019.01)
(Continued)

(52) U.S. Cl.
CPC .............. *G16B 5/20* (2019.02); *G06N 20/00* (2019.01); *G16B 25/10* (2019.02); *G16H 20/10* (2018.01); *G16H 50/50* (2018.01)

(58) Field of Classification Search
None
See application file for complete search history.

(56) References Cited

U.S. PATENT DOCUMENTS

| | | |
|---|---|---|
| 2010/0004257 A1 | 1/2010 | Haura |
| 2013/0184999 A1 | 7/2013 | Ding |

(Continued)

FOREIGN PATENT DOCUMENTS

| | | | | |
|---|---|---|---|---|
| WO | WO-2019165366 A1 | * | 8/2019 | |
| WO | WO-2020113237 A1 | * | 6/2020 | .......... A61B 5/4836 |

OTHER PUBLICATIONS

"Network-based Biased Tree Ensembles (NetBiTE) for Drug Sensitivity Prediction and Drug Sensitivity Biomarker Identification in Cancer", Ali Oskooei, Matteo Manica, Roland Mathis and María Rodríguez Martínez, arXiv:1808.06603 [q-bio.QM], Aug. 18, 2018.
A review of ensemble methods in bioinformatics Yang et al., Curr. Bioinforma. Dec. 2010, 5(4), pp. 296 to 308.

(Continued)

*Primary Examiner* — Rajesh Khattar
*Assistant Examiner* — Andrew E Lee
(74) *Attorney, Agent, or Firm* — Richard B. Thomas

(57) ABSTRACT

A machine learning model is generated for drug efficacy prediction in treatment of genetic disease from a dataset correlating gene expression data for disease-cell samples with drug efficacy values for the samples. Bias weights are stored that correspond to respective genes in the samples. Each bias weight is dependent on predetermined relevance of the respective gene to drug efficacy. The model is generated by processing the dataset via a tree ensemble method wherein decision trees are grown with splits corresponding to respective genes in the samples. The gene for each split is chosen from a respective subset of the genes, and genes are selected for inclusion in this subset with respective probabilities dependent on the corresponding bias weights. The model is stored, and can be applied to gene expression data measured for a patient to obtain a personalized drug efficacy prediction for devising a personalized course of treatment.

19 Claims, 7 Drawing Sheets

(51) Int. Cl.
  *G16B 5/20*     (2019.01)
  *G16B 25/10*    (2019.01)
  *G16H 20/10*    (2018.01)

(56)            References Cited

U.S. PATENT DOCUMENTS

| 2015/0220838 | A1  | 8/2015 | Martin et al. |               |
|--------------|-----|--------|---------------|---------------|
| 2016/0041153 | A1* | 2/2016 | Brown         | G01N 33/5308  |
|              |     |        |               | 436/501       |
| 2016/0246919 | A1* | 8/2016 | Wang          | G06Q 10/04    |
| 2019/0034581 | A1* | 1/2019 | Aliper        | G16B 40/20    |

OTHER PUBLICATIONS

Breiman L. "Random Forests", L. Breiman, Mach Learn [Internet] Jan. 2001, 45, http://dx.doi.org/10.1023/A:1010933404324.

"CART: classification and regression trees", Steinberg & Colla, Top Ten Algorithms Data Min. Jan. 2009, 9:179.

Fei Zhang, Minghui Wang, Jianing Xi, Jianghong Yang, and Ao Li "A Novel Heterogeneous Network-Based Method for Drug Response Prediction in Cancer Cell Lines" Feb. 20, 2018.

Raziur Rahman, Kevin Matlock, Souparno Ghosh and Ranadip Pal "Heterogeneity Aware Random Forest for Drug Sensitivity Prediction" Sep. 12, 2017.

Hussein Hijazi, Ming Wu, Aritro Nath, and Christina Chan "Ensemble Classification of Cancer Types and Biomarker Identification" Sep. 2014 2014.

* cited by examiner

DRUG EFFICACY PREDICTION FOR TREATMENT OF GENETIC DISEASE

STATEMENT REGARDING PRIOR DISCLOSURES BY THE INVENTOR OR A JOINT INVENTOR

The following disclosure is submitted under 35 U.S.C. 102(b)(1)(A): "Network-based Biased Tree Ensembles (NetBiTE) for Drug Sensitivity Prediction and Drug Sensitivity Biomarker Identification in Cancer", Ali Oskooei, Matteo Manica, Roland Mathis and Maria Rodriguez Martinez, arXiv:1808.06603 [q-bio.QM], 18 Aug. 2018.

BACKGROUND

The present invention relates generally to drug efficacy prediction for treatment of genetic disease, and more particularly to generation and use of machine learning models for drug efficacy prediction in such treatment.

Typically, a genetic disease is not one disease but rather a collection of related diseases. Different patients suffering from a single type of cancer, for example, may have different genetic mutations and, potentially, need a different course of treatment. There is strong evidence that tumor's genetic makeup can influence the outcome of anti-cancer drug treatment resulting in heterogeneity in clinical response of various subjects to a certain drug. This has led to the promise of personalized (or precision) medicine where molecular biomarkers, e.g. gene expression data, obtained from a patient may be used to design a personalized course of treatment.

Large datasets have emerged linking genomic profiles to efficacy of pharmaceutical drugs. Such datasets correlate gene expression data of different disease-cell samples with measured drug efficacy values, e.g. half maximal inhibitory concentration ($IC_{50}$) values, and thus indicate sensitivity of disease cells with various genetic characteristics to particular pharmaceutical drugs. Machine learning can be used to harness this data in the interests of precision medicine. Machine learning provides techniques for processing (often massive) datasets from a real-word application in relation to a basic model for the application in order to train, or optimize, the model for the application in question. The model can then be applied to perform tasks based on new (unseen) data generated in that application.

SUMMARY

According to at least one embodiment, there is provided a computer-implemented method. The method includes generating a machine learning model for drug efficacy prediction in treatment of genetic disease from a dataset correlating gene expression data for disease-cell samples with drug efficacy values for the samples. The generating the machine learning model includes storing bias weights corresponding to respective genes in the samples. Each bias weight is dependent on predetermined relevance of the respective gene to drug efficacy. The method further includes generating the model by processing the dataset via a tree ensemble method wherein decision trees are grown with splits corresponding to respective genes in the samples. The gene for each split is chosen from a respective subset of the genes, and genes are selected for inclusion in this subset with respective probabilities which are dependent on the corresponding bias weights. The method further comprises storing the model for prediction of drug efficacy values based on gene expression data of patients.

At least one additional embodiment provides a computer program product comprising a computer readable storage medium embodying program instructions, executable by a computing system, to cause the computing system to perform a method for generating a machine learning model for drug efficacy prediction as described above.

At least one further embodiment provides a drug efficacy prediction method for use in treatment of genetic disease of a patient. The method includes making gene expression measurements for the patient to obtain gene expression data, and performing a computer-implemented method to generate a machine learning model as described above. After storing the model, the method further comprises applying the model to the gene expression data of the patient to obtain a drug efficacy prediction for that patient, and outputting the drug efficacy prediction for use in treatment of the patient.

At least one further embodiment is a computing apparatus comprising one or more processors and a memory having computer readable code thereon, wherein the one or more processors, in response to retrieval and execution of the computer readable code cause the computing apparatus to perform operations comprising generating a machine learning model for drug efficacy prediction in treatment of genetic disease from a dataset correlating gene expression data for disease-cell samples with drug efficacy values for the samples. The generating the machine learning model includes storing bias weights corresponding to respective genes in the samples, where each bias weight is dependent on predetermined relevance of the respective gene to drug efficacy, and includes generating the model by processing the dataset via a tree ensemble method wherein decision trees are grown with splits corresponding to respective genes in the samples. The gene for each split is chosen from a respective subset of the genes, and genes are selected for inclusion in this subset with respective probabilities which are dependent on the corresponding bias weights. The operations further comprise storing the model for prediction of drug efficacy values based on gene expression data of patients.

Additional embodiments will be described in more detail below, by way of illustrative and non-limiting example, with reference to the accompanying drawings.

DETAILED DESCRIPTION

Figure 1:
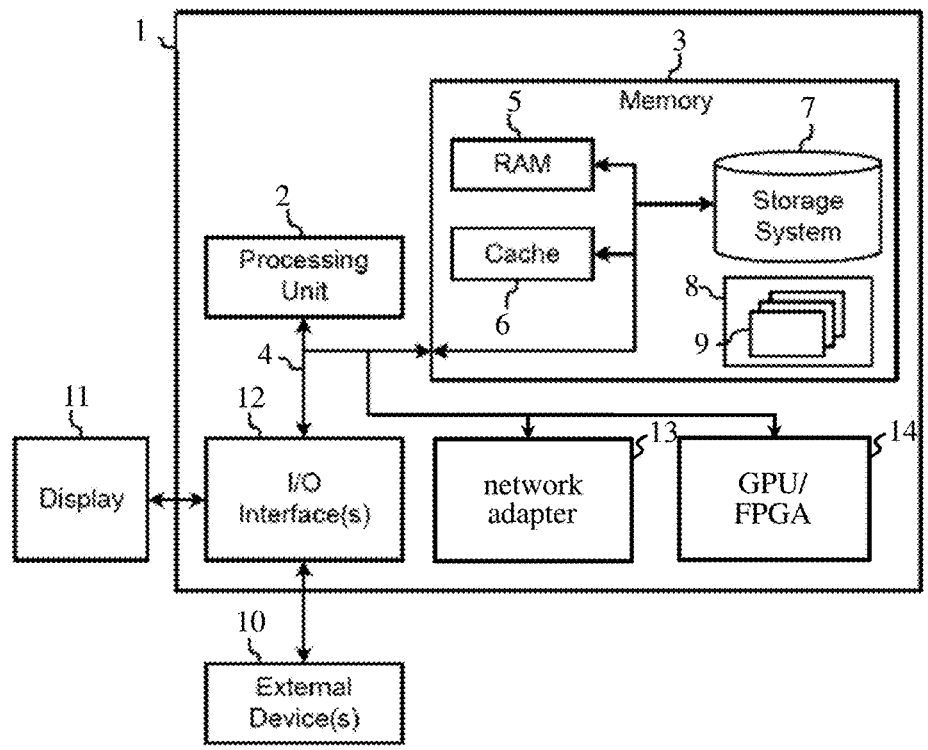
FIG. 1 is a schematic representation of a computer for implementing model generation and drug efficacy prediction methods embodying possible examples of embodiments.

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments to be described may be performed as computer-implemented methods for generating machine learning models for drug efficacy prediction in treatment of genetic disease. The methods may be implemented by a computing system comprising one or more general- or special-purpose computers, each of which may comprise one or more (real or virtual) machines, providing functionality for implementing the operations described herein. Steps of methods embodying example embodiments may be implemented by program instructions, e.g. program modules, implemented by a processing apparatus of the system. Generally, program modules may include routines, programs, objects, components, logic, data structures, and so on that perform particular tasks or implement particular abstract data types. The computing system may be implemented in a distributed computing environment, such as a cloud computing environment, where tasks are performed by remote processing devices that are linked through a communications network. In a distributed computing environment, program modules may be located in both local and remote computer system storage media including memory storage devices.

FIG. 1 is a block diagram of exemplary computing apparatus for implementing methods embodying possible examples of embodiments. The computing apparatus is shown in the form of a general-purpose computer 1. The components of computer 1 may include processing apparatus such as one or more processors represented by processing unit 2, a system memory 3, and a bus 4 that couples various system components including system memory 3 to processing unit 2. The processing unit 2 may be or comprise one or more general purpose (or embedded or digital signal) processors, application specific integrated circuits, programmable logic devices, integrated circuits, other circuitry, or some combination of these.

Bus 4 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer 1 typically includes a variety of computer readable media. Such media may be any available media that is accessible by computer 1 including volatile and non-volatile media, and removable and non-removable media. For example, system memory 3 can include computer readable media in the form of volatile memory, such as random access memory (RAM) 5 and/or cache memory 6. Computer 1 may further include other removable/non-removable, volatile/non-volatile computer system storage media. By way of example only, storage system 7 can be provided for reading from and writing to a non-removable, non-volatile magnetic medium (commonly called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can also be provided. In such instances, each can be connected to bus 4 by one or more data media interfaces.

Memory 3 may include at least one program product having one or more program modules that are configured to carry out functions of embodiments of the invention. By way of example, program/utility 8, having a set (at least one) of program modules 9, may be stored in memory 3, as well as an operating system, one or more application programs, other program modules, and program data. Each of the operating system, one or more application programs, other program modules, and program data, or some combination thereof, may include an implementation of a networking environment. Program modules 9 generally carry out the functions and/or methodologies of embodiments of the invention as described herein.

Computer 1 may also communicate with: one or more external devices 10 such as a keyboard, a pointing device, a display 11, etc.; one or more devices that enable a user to interact with computer 1; and/or any devices (e.g., network card, modem, etc.) that enable computer 1 to communicate with one or more other computing devices. Such communication can occur via Input/Output (I/O) interfaces 12. Also, computer 1 can communicate with one or more networks such as a local area network (LAN), a general wide area network (WAN), and/or a public network (e.g., the Internet) via network adapter 13. As depicted, network adapter 13 communicates with the other components of computer 1 via bus 4. Computer 1 may also communicate with additional processing apparatus 14, such as a GPU (graphics processing unit) or FPGA (field programmable gate array), for implementing embodiments. It should be understood that although not shown, other hardware and/or software components could be used in conjunction with computer 1. Examples include, but are not limited to: microcode, device drivers, redundant processing units, external disk drive arrays, RAID systems, tape drives, and data archival storage systems, etc.

In embodiments below, machine learning models for drug efficacy prediction in treatment of genetic disease are generated by processing a training dataset. The training dataset correlates measured gene expression data for disease-cell samples with measured drug efficacy values for the samples. The models are generated by processing the dataset via a tree ensemble method in which multiple decision trees are grown to fit the gene expression data in the dataset to the measured drug efficacy values in an optimized manner. The resulting model, or tree ensemble, can then be applied to new (unseen) gene expression data to predict drug efficacy values for that data. Tree ensemble methods, such as the popular random forests method, are well known in the art (see e.g.: "A review of ensemble methods in bioinformatics", Yang et al., Curr. Bioinforma. 2010, 5 (4), pp. 296 to 308; and Breiman L. "Random Forests", L. Breiman, Mach Learn [Internet] 2001, 45, http://dx.doi.org/10.1023/A:1010933404324) and need not be described in detail here. However, some basic principles are described below to assist understanding of the embodiments to follow.

Decision trees (often called "CART trees"—see "CART: classification and regression trees", Steinberg & Colla, Top Ten Algorithms Data Min. 2009, 9:179) are grown by repeatedly splitting samples in a training dataset into subsets based on attributes associated with features of the samples. (In the embodiments below, features correspond to genes in disease-cell samples and the attributes are measured gene expression values for these genes). The splits correspond to branches of the tree, and each branch indicates whether the sample attribute associated with the feature selected for a split satisfies a specified condition. Branches are repeatedly split to grow the tree until a predefined stop condition is satisfied. A stop condition may specify, for example, a maximum number of samples in the subsets at the leaves of the tree (i.e. the subsets resulting from the last splits in each branch). Alternatively, for example, the stop condition may relate to the variance (or sum-of-squares) of the target values of the leaf subsets. Spitting may be stopped, for instance when the decrease in variance of the subsets due to a split is less than a defined threshold. Split features, and their associated split conditions, are selected via an optimization algorithm based on analysis of the resulting subsets. For classification trees, where the target values are a set of discrete values corresponding to respective categories ("classes") of samples, optimization can be based on enhancing "purity" of the subsets as measured by the distribution of classes in the subsets, e.g. by Gini impurity. For regression trees where the target values can be continuous values (e.g. real numbers), optimization can be based on minimizing variance of the resulting subsets. In effect, the aim is to select splits such that samples in the resulting subsets are quite similar to each other (e.g. have low variance or sum-of-squares). Splitting can continue in this way, e.g. minimizing variance, until the extreme case where each leaf subset contains only one sample (and hence the variance is zero), or some other stop condition is satisfied. The depth of a tree, as determined by the number of successive splits, is effectively a tuning parameter that can be varied as desired for a given modeling operation. The tree generation procedure is explained further below with reference to FIG. 2.

Figure 2:
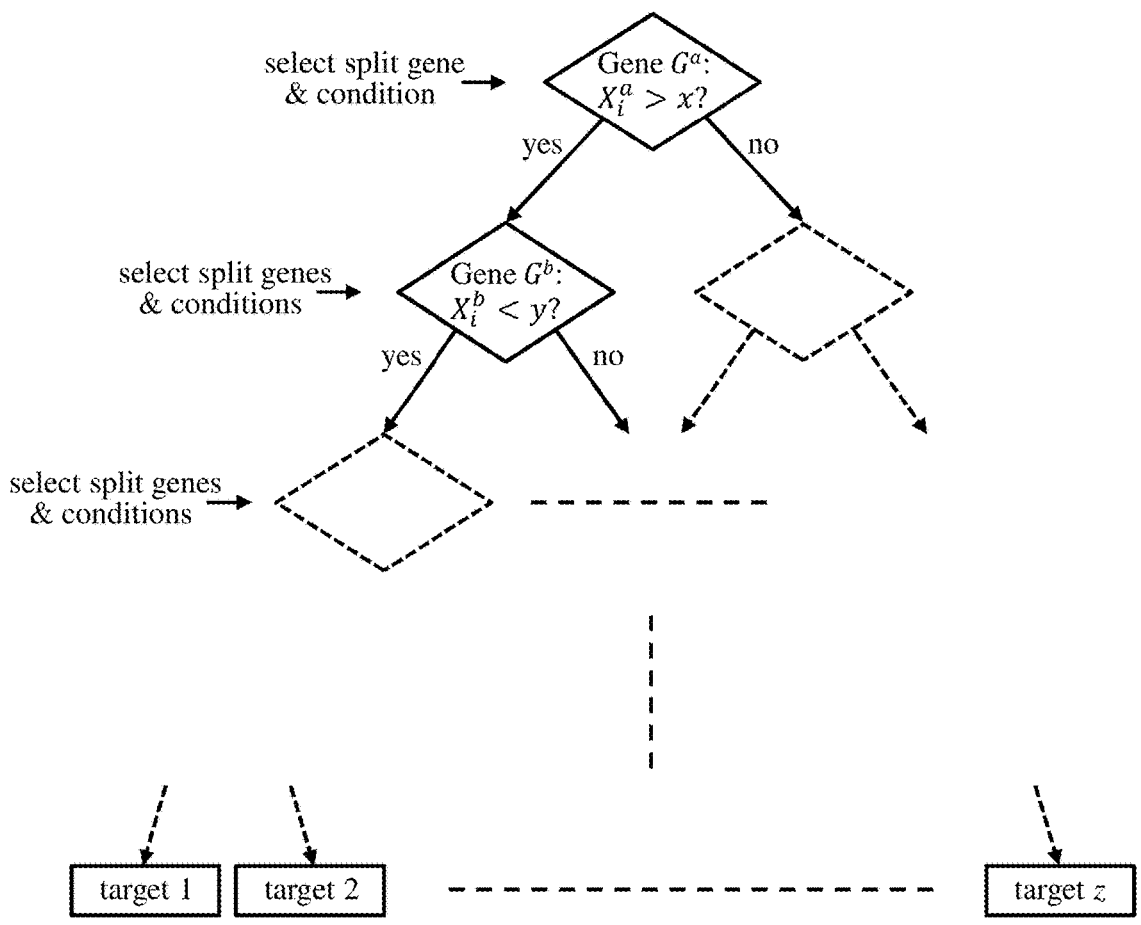
FIG. 2 illustrates basic principles involved in growing decision trees for machine learning model generation.

FIG. 2 is a simple schematic illustrating basic principles of a decision tree generation process for an exemplary training dataset. The dataset, shown at the top 201 of the figure, comprises n training samples labelled $S_i$, i=1 to n. Each sample $S_i$ contains attribute values $X_i^j$, j=1 to m, for a plurality m of features, and a target value $V_i$ for the sample. In this example, in accordance with embodiments below, the m features correspond to genes, labelled $G^i$, in disease-cell samples and the attributes $X_i^j$ represent measured gene expression values for respective genes. These gene expression values comprise measurements relating to the individual genes, and in particular the functional products of these genes, in the cell samples. Typically, gene expression data comprises relative (with respect to a control sample) mRNA abundance measurements for mRNAs transcribing every gene within a sample (i.e. a cell). The target values $V_i$ represent measured drug efficacy values for the corresponding samples. In embodiments below, drug efficacy is measured via $IC_{50}$ values which indicate drug concentration required to achieve 50% of the drug's maximum inhibitory effect (on a gene product for instance). While $IC_{50}$ values are widely used as a measure of drug efficacy, in general any measurement values indicating sensitivity of genetic processes to a drug may be used as drug efficacy values.

A decision tree for the dataset can be grown with nodes and splits as illustrated in the lower portion 202 of FIG. 2. A sample feature, here a gene $G^a$, is selected as the split feature for a first split, and an attribute condition (here whether a measurement value $X_i^a$ for gene $G^a$ is greater than a specified value x) is defined for the split. The gene, and the associated attribute condition, selected for the split are chosen from the possible options by optimization of a predetermined loss function. For the regression example here and in embodiments below, the split gene and condition are selected to minimize variance of the target values in the two sample subsets generated by the split. The process is then repeated in each branch of the split. That is, for each subset (containing samples with $X_i^a > x$, or $X_i^a \leq x$) a gene and attribute condition are selected for further splitting that subset. This process continues along all branches until a predetermined stop condition is satisfied as described above. The resulting subsets determine the target values at the leaves, denoted by target 1, target 2, . . . , target z in the figure. For example, if the stop condition specifies a "target partition size" (i.e. a maximum number of samples in the leaf subsets) equal to one, the target value in a leaf will be the drug efficacy value of the single sample in the corresponding subset. For target partition sizes greater than one, target values in the leaves may correspond to ranges of values, or average (e.g. mean) values for the leaf subsets. The resulting decision tree can then be applied to predict target values for a new (unseen) sample by applying the split conditions defined in the tree to the attribute values of the new sample to reach the applicable target value in the tree.

While basic principles involved in growing decision trees are described for a simple example above, the procedure can be highly complex in practice. Tree ensemble methods such as the random forests (RF) method generate multiple decision trees to model a training dataset, and an output of the resulting model (tree ensemble) is given as the mean prediction (for regression) or mode of the classes (for classification) obtained from the individual trees. In the RF method, for each split in a decision tree, a subset (d<m) of the total number m of features is selected at random to be considered as split features. For typical datasets with large numbers of features, the process of optimizing the split outcomes over all features in the subsets can be extremely compute-intensive. Significant processing resources, typically provided by powerful multi-core CPUs (central processing units), often with accelerator units such as GPUs (graphics processing units) and/or FPGAs (field-programmable gate arrays), are required for practical implementation.

Figure 3:
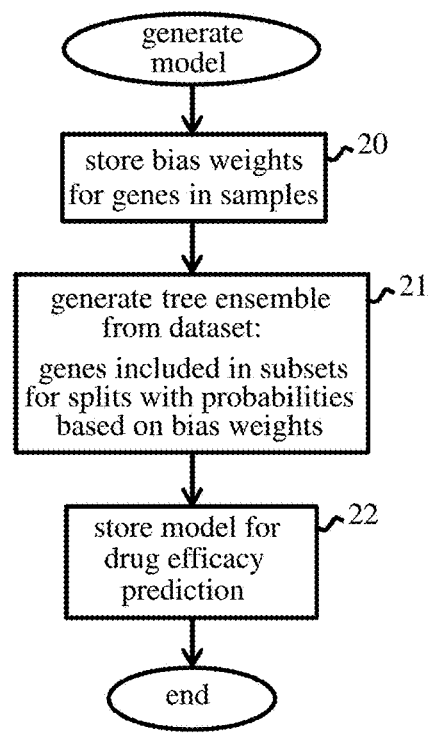
FIG. 3 indicates steps of a first model generation method embodying additional example embodiments.

FIG. 3 indicates steps of a first method in an example of an embodiment for generating a machine learning model for drug efficacy prediction. The method can be implemented by a computing system 1 using a training dataset which may be stored locally, in memory 3 of the computing system, or stored remotely and accessed by system 1 via a network. The training dataset correlates gene expression data for disease-cell samples with drug efficacy values for the samples as described above. The method employs a set of bias weights, corresponding to respective genes in the cell samples, which is stored in memory 3 of system 1. Each bias weight in this set is dependent on predetermined relevance of the respective gene to drug efficacy. Relevance of a gene to efficacy of a pharmaceutical drug is determined based on prior knowledge, e.g. obtained from published literature, experimental results, computational analysis, data mining, etc., indicating known or predicted sensitivity of genetic characteristics to action of a particular drug. For example, a gene (or more particularly a gene whose functional product) is a known drug target can be deemed highly relevant to efficacy of the drug. Similarly, genes having known/predicted interactions or effects on a drug target gene may be considered relevant to drug efficacy here. Bias weights are assigned to genes in the cell samples according to their relevance as determined from the prior knowledge sources, e.g. with relevant genes being assigned a higher bias weight than non-relevant genes. For example, each bias weight may be selected as one of two values, a higher value and a lower value, dependent on predetermined relevance and non-relevance respectively of the corresponding gene to drug efficacy. The bias weights thus defined based on prior knowledge are stored in memory 3 of system 1 in step 20 of FIG. 3.

Step 21 of FIG. 3 represents the model generation process. In this step, the model is generated by processing the training dataset via a tree ensemble method. The decision trees of the tree ensemble are grown with splits corresponding to respective genes in the cell samples, generally as described with reference to FIG. 2. The gene for each split is chosen from a respective subset of genes in the samples. This is similar to the standard RF method described above. However, unlike that method, genes are selected for inclusion in the subset for a split with respective probabilities which are dependent on the corresponding bias weights stored in step 20. For example, where higher bias weights indicate higher relevance, the selection probability will be higher for genes with higher bias weights. (Translation of bias weights into selection probabilities for generating the split subsets can be achieved using standard techniques well-known to those skilled in the art. For instance, a softmax function may be used to derive a probability distribution from a set of weights. This ensures that all values are between 0 and 1 and the summation of all values equals 1). The resulting model, comprising the tree ensemble generated in step 21, is stored in system 1 in step 22 for subsequent prediction of drug efficacy values based on gene expression data of individual patients.

Figure 4:
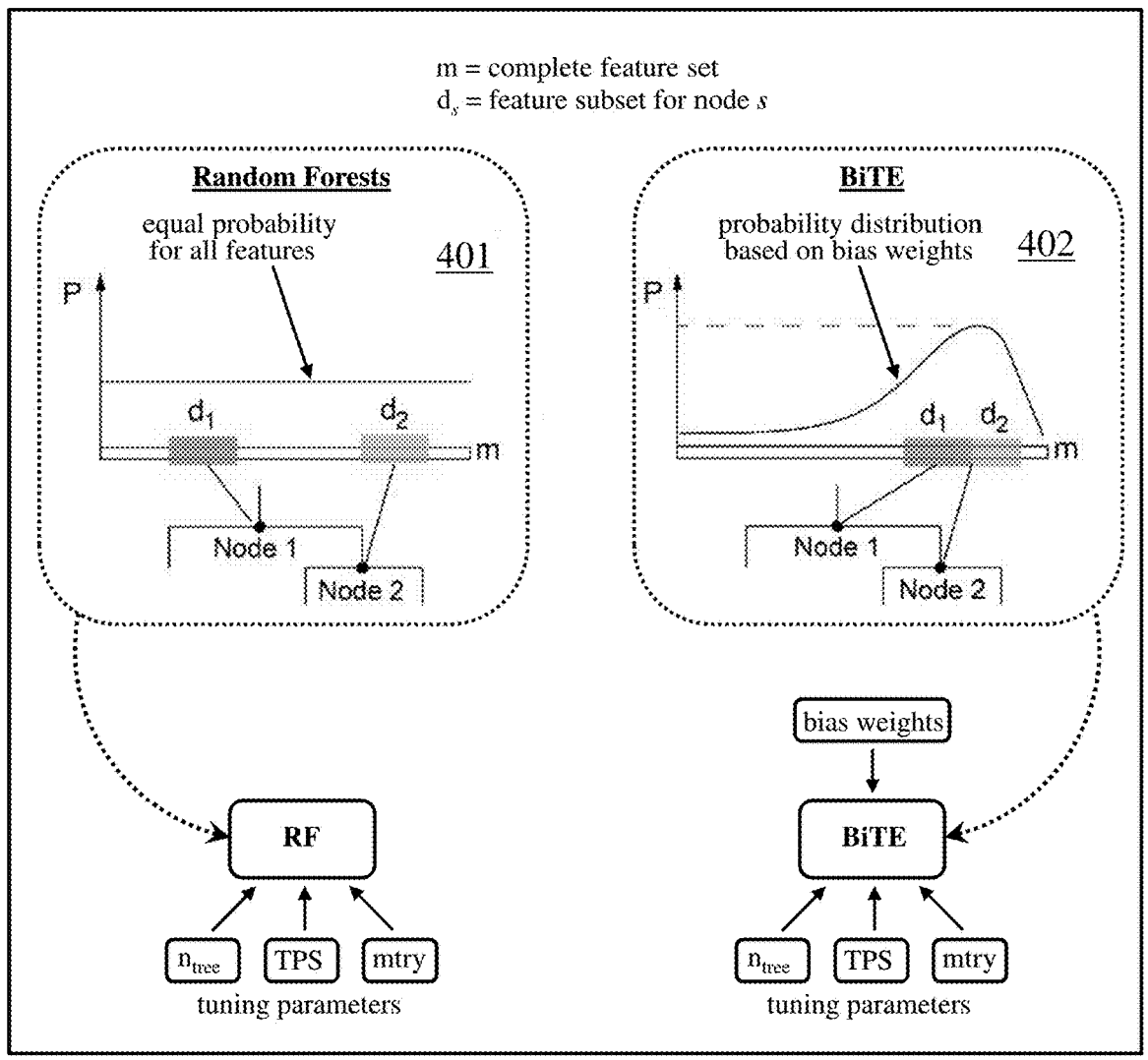
FIG. 4 is a schematic diagram comparing operation of the FIG. 3 method with a prior method.

The above method thus employs a tree ensemble technique similar to the RF method but introduces a bias into selection of the genes which are included in the subsets for the splits. Genes are selected for inclusion in these subsets in a probabilistic manner, and the selection probabilities are dependent on bias weights based on prior knowledge of gene relevance to drug efficacy. The schematic of FIG. 4 highlights this key difference between the biased tree ensemble (BiTE) method of FIG. 3 and the RF approach. In the RF method 401 on the left of the figure, features included in the feature subset $d_s$ for a node s are selected from the complete set of m features at random, and thus with equal probability P. In the BiTE method 402 on the right, the probabilities of individual features being included in a subset $d_s$ follow a probability distribution determined by the bias weights, with relevant features (here with higher weights) being selected with higher probability than non-relevant features (with lower weights). This biases the subsets, and hence selection of a split feature in the trees, towards more relevant features as determined by the bias weights.

By biasing the split-feature selection using bias weights based on informative prior knowledge, the BiTE method offers significant performance gains at substantially lower computational cost compared to the RF approach. Apart from the bias weights in BiTE, both techniques use the same set of three tuning parameters indicated in the figure: $n_{tree}$ (number of decision trees in the ensemble); TPS (target partition size explained above); and mtry (number of features in the subsets $d_s$). Higher $n_{tree}$ improves model performance and stability but requires more computation. TPS defines the depth of the trees and can control over- or under-fitting. A larger mtry improves model performance but significantly increases computational cost, particularly for datasets with large numbers of features as is typical of biological datasets. The BiTE method offers significantly improved model accuracy with much lower mtry and $n_{tree}$ values than RF as demonstrated by examples below. Embodiments herein offer highly efficient model generation methods for drug efficacy prediction, allowing more accurate models to be generated efficiently with significantly reduced processing resources.

Figure 5:
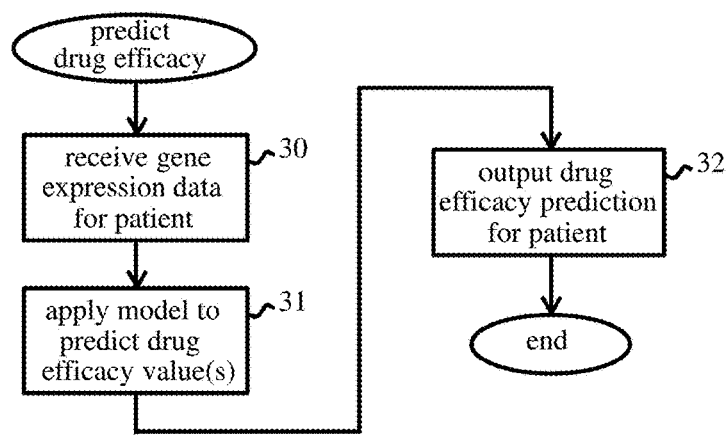
FIG. 5 indicates steps of a drug efficacy prediction method embodying another example of an embodiment.

Models generated by methods embodying the techniques presented herein offer enhanced accuracy in drug efficacy prediction for individual patients and formulation of personalized treatment plans. Basic steps involved in predicting drug efficacy for a particular patient are indicated in the flow diagram of FIG. 5. After generating and storing the model as described above, the gene expression data measured for a patient is input to computing system 1. This gene expression data is obtained in known manner by analyzing a disease-cell sample obtained from the patient. For a patient suspected to suffer from a certain type of cancer, for example, tumor biopsy is generally performed to obtain the gene expression data. The patient's gene expression data is received by system 1 in step 30 of FIG. 5. In step 31, the system applies the pre-stored model to this gene expression data to obtain a drug efficacy prediction for that patient. The drug efficacy prediction indicates the output of the model for the patient's gene expression data. This output can be expressed as a function of the target values obtained from all trees in the ensemble with the patient's data, for example as an average (e.g. mean or median) of the target values to provide a predicted efficacy value for the drug in question and that particular patient. In step 32, the drug efficacy prediction is output by system 1 for use in treatment of the patient. Such predictions may be used, for example, to select a particular drug therapy and/or determine drug dosages appropriate to a patient. As explained further below, models for exemplary embodiments can be generated for multiple drugs. Drug efficacy predications obtained from such models can provide results for more than one drug, allowing efficacy comparisons and formulation of treatment plans personalized to individual patients.

Figure 6A:
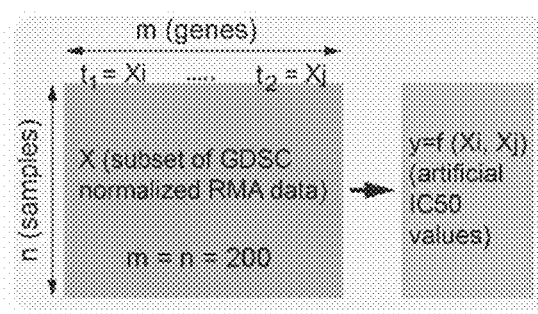
FIGS. 6a and 6b illustrate features of an exemplary implementation of the FIG. 3 method.
Figure 6B:
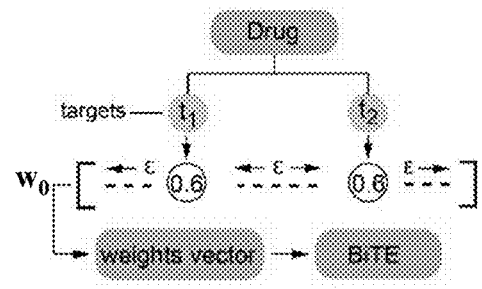
Figure 7A:
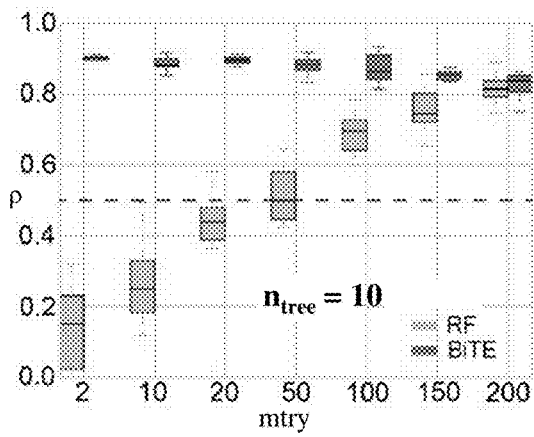
FIGS. 7a through 7d illustrate results obtained with the implementation of FIGS. 6a and 6b.
Figure 7B:
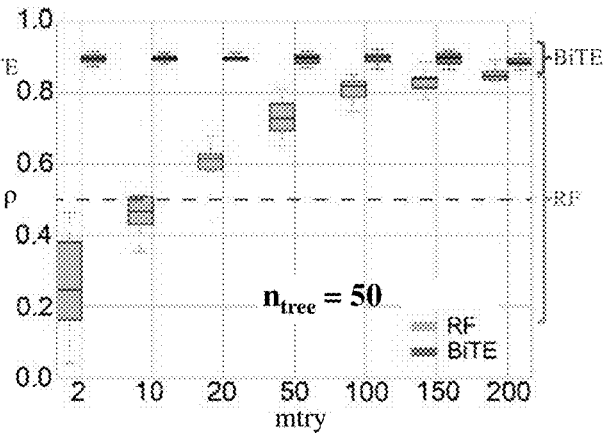
Figure 7C:
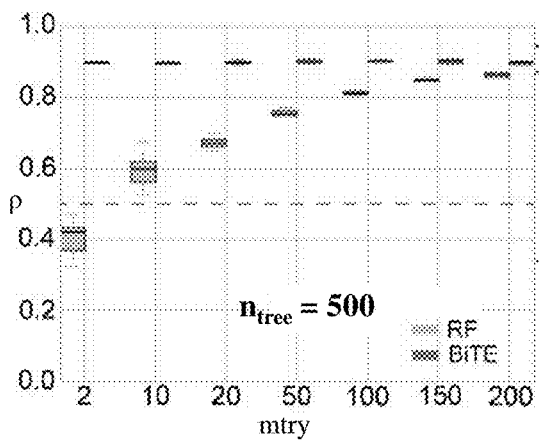
Figure 7D:
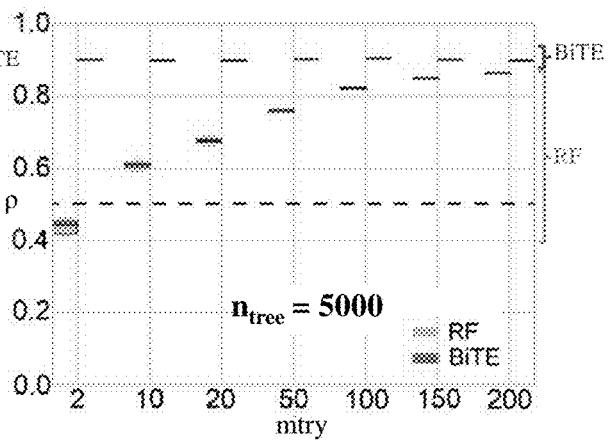

An exemplary implementation of the above embodiment is illustrated schematically in FIGS. 6a and 6b. As indicated in FIG. 6a, this implementation used an artificial dataset created by randomly selecting a subset of 200 cell lines and 200 genes from the standardized RMA (robust multi-array analysis) basal expression profiles within the GDSC (Genomics of Drug Sensitivity in Cancer) dataset, and generating synthetic $IC_{50}$ values as a non-linear function ($y=f(X_i, X_j)$) of two randomly selected drug target genes (denoted here by $t_1=X_i$ and $t_2=X_j$) according to the following 5th degree relationship:

$$IC_{50}=aX_i^5+bX_j^5+cX_i^3X_j^2+dX_i^2X_j^3 i,j, \in \{\mathbb{N} <200\}. \quad (1)$$

As indicated in FIG. 6b, bias weights W were assigned to each of the 200 genes to define a weights vector $w_0$ in which W=0.6 was assigned to the two drug target genes (where W=0 corresponds to "never select" and W=1 corresponds to "always select") and a small positive weight ($\varepsilon=1e-5$, or $10^{-5}$) was assigned to all other genes. The weights vector was used in the BiTE method to generate a model for the dataset. The resulting model was applied to predict $IC_{50}$ values for unseen test samples, and model performance was assessed against synthetic $IC_{50}$ values derived as described above for the test samples. The model performance was evaluated by determining the Pearson correlation (the square root of the coefficient of determination) p between the actual $IC_{50}$ values and the predicted ones. Models were generated in this way with values of mtry ranging from 2 (the number of targets) to 200 (the full set of genes), and for different numbers of trees $n_{tree}$, and performance was compared with that of the RF method.

The performance results for $n_{tree}$=10, 50, 500 and 5000 are shown in FIGS. 7a, 7b, 7c and 7d respectively. Results for the RF and BiTE methods are indicated by light grey and dark grey respectively, and the dashed line indicates a linear regression model performance as a baseline comparison. It can be seen that the BiTE method consistently outperforms RF, and dramatically so at low numbers of trees and low mtry values. It is expected that the highest mtry values will perform best due to the opportunity to investigate each and every gene and find the most informative features. The figures show that the BiTE method achieves the same maximal performance with a minimal mtry of 2, even with a small number of trees ($n_{tree}=10$). Improved accuracy is thus achieved with a significant saving in computational cost.

Although the above implementation used an ideal dataset, the results indicate that a clear improvement in model performance and efficiency can be achieved over standard RF models by biasing split feature selection towards relevant genes based on prior knowledge. Introduction of this bias significantly reduces the optimization required to train the model. Moreover, BiTE models are more transparent and interpretable compared to RF as it is immediately clear which set of features contributed the most to model performance. For instance, if a set of (high-bias) features results in loss of BiTE model accuracy, it can be deduced that those features were uninformative predictors; conversely, an improved accuracy can be attributed to the set of features towards which the model was biased. Hence, the BiTE method can be used to examine predictive power of various features in a transparent and controllable manner. In this manner, BiTE models can be used to identify genes which correspond to important biomarkers for drug sensitivity.

The foregoing embodiment offers improved model efficiency even with a simple weights vector comprising bi-valued bias weights. However, embodiments can be envisaged where bias weights can take more than two values dependent on the expected degree of relevance of particular genes to drug efficacy. Moreover, while the model is generated for a single drug above, the technique can be readily adapted to accommodate multiple drugs. In particular, bias weights can be stored for each of a plurality of drugs, and a model accommodating all drugs can be generated as a set of sub-models, one for each drug, where the sub-model for each drug is generated via the tree-ensemble method described using selection probabilities dependent on the bias weights for that drug.

Figure 8:
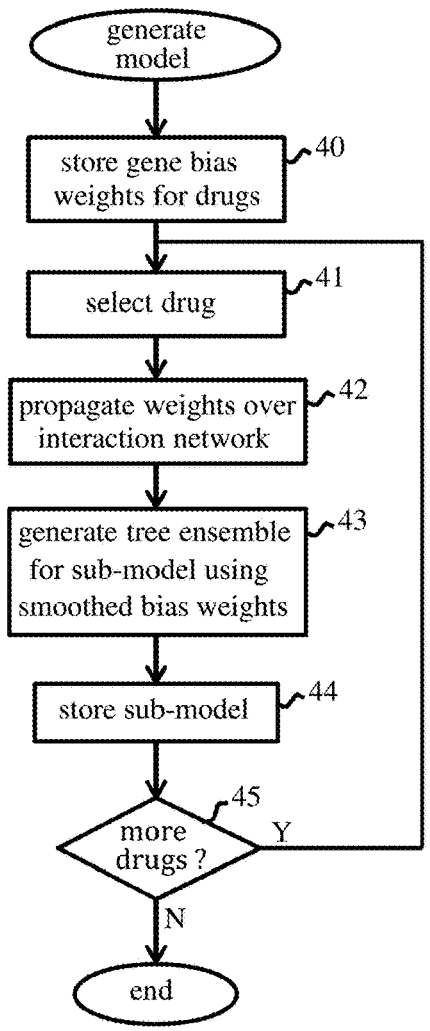
FIG. 8 indicates steps of a second model generation method embodying an exemplary embodiment.

An example of an embodiment of the model generation method will now be described with reference to FIG. 8. This method generates a series of sub-models to accommodate multiple drugs, and includes an additional processing step to inject an additional level of prior knowledge into the model. For each of the drugs addressed by the model, a set of bias weights is defined as described above and stored in system 1 in step 40. In step 41, the system selects a first drug for sub-model generation. In step 42, the system retrieves the set of bias weights for the selected drug, and propagates these weights over a predetermined network, indicating interaction between genes in the training samples, to obtain respective smoothed bias weights. The network used here may be the STRING protein-protein interaction network, or other similar network, which defines interactions between genes (or more particularly gene-products such as proteins), represented by nodes in a network over which values can be propagated and modified (smoothed) based on interactions between nodes as defined in the network. Such networks of molecular interactions can be obtained from a variety of sources, and may be pre-stored in system 1 or accessed remotely for the propagation step. The weight propagation results in a smoothed weight distribution where neighbors of a drug target gene are also assigned a high weight. The output of the propagation step is a set of smoothed bias weights for respective genes in the training samples, and the resulting smoothed weights vector is stored in system 1. In step 43, a sub-model for the current drug is generated via a tree ensemble method as previously described. Here, however, the selection probabilities for generating the split subsets are dependent on the smoothed bias weights for respective genes. The resulting tree ensemble for the sub-model is stored in step 44. In decision step 45, the system checks whether any further drugs remain to be accommodated in the model. If so, ("Yes" (Y) at decision block 45), then operation reverts to step 41. The next drug is selected and steps 42 to 44 are repeated to generate a sub-model for this drug. When sub-models have been stored for all drugs ("No" (N) at decision block 45), operation is complete. The resulting model thus consists of a set of sub-models for the drug-set in question. This model can be applied to individual patients' gene expression data as previously described. The sub-models can be applied to the gene expression data in a pipelined manner to output a drug efficacy prediction indicating predicted drug efficacy values for all drugs in the set. This can then be used to select a particular treatment personalized to the patient.

The above method offers enhanced accuracy for drug efficacy prediction through injection of an additional layer of prior knowledge via the network propagation of bias weights. The propagation of the bias weights defines neighborhoods of influence around the drug targets, and as such simulates the spread of perturbations within the cell following drug administration. An exemplary implementation of this network-based biased tree ensemble (NetBiTE) method is described in more detail below.

Figure 9:
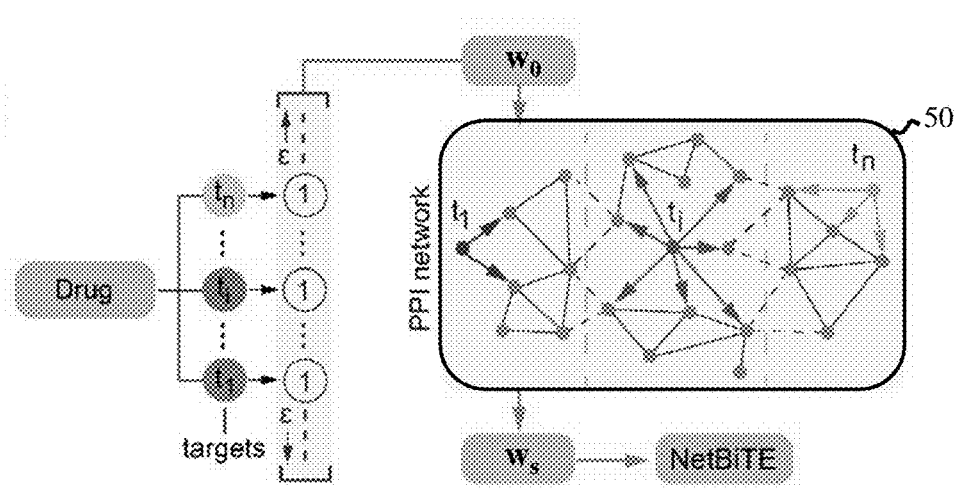
FIG. 9 illustrates features of an exemplary implementation of the FIG. 8 method.

The NetBiTE method was applied to the GDSC dataset for a set of 50 cancer drugs. The initial weighting and propagation scheme is illustrated schematically in FIG. 9. For each drug, an initial bias weight of $W_0=1$ was given to each drug target and weight of $W_0=\varepsilon=1e-5$, or $10^{-5}$ was assigned to all other genes. The resulting weights vector $w_0$ was smoothed by propagation over the STRING PPI (protein-protein interaction) network as indicated schematically at 50. The network smoothing of the weights can be described as a random walk and propagation of the initial weights $W_0$ throughout the network from a neighbor to the next. We denote the string network as $S=(P, E, A)$ where P are the protein vertices of the network, E are the edges between the proteins and A is the weighted adjacency matrix. The smoothened weights are determined iteratively from the following function:

$$W_{t+1} = \alpha W_t A' + (1-\alpha) W_0 A' = D^{-1/2} A D^{-1/2}, \quad (2)$$

where A' is the normalized adjacency matrix in which the weight for each edge is normalized by the degrees of its end points, resulting in the probability of an edge existing between two nodes in a random walk over the network. D is a diagonal matrix with the row sums of the adjacency matrix on the diagonal. The diffusion tuning parameter, a ($0<\alpha<1$), defines the distance that the prior knowledge weights can diffuse through the network. The optimal value of $\alpha=0.7$ reported for the STRING network was adopted. Adopting a convergence rule of $e=(W_{t+1}-W_t)<1e-6$ (that is, $10^{-6}$), we solved equation (2) iteratively for the initial weight vector associated with each drug to obtain the resulting smoothed weight vector $w_s$. The propagation results in lower-than-initial weights for the targets (W<1) and positive weights for all other genes within the network (W>0). The smoothed weight vector ($w_s$) was then used to generate the NetBiTE model, and $IC_{50}$ values for each drug were then predicted for unseen samples from the dataset. Model performance was compared with the RF method for various values of $n_{tree}$. The parameter mtry was set to the number of reported targets for each drug. A TPS of 1 was used for all models, and $IC_{50}$ drug response data was scaled between zero and one.

Figure 10:
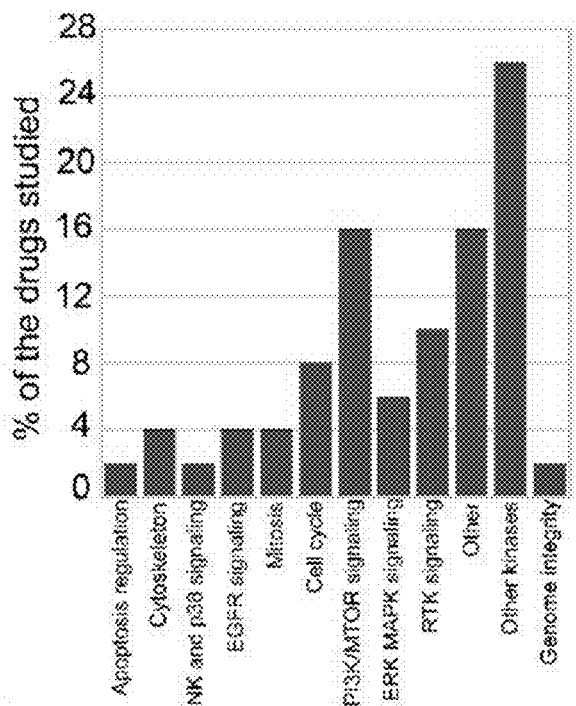
FIGS. 10 through 12 illustrate results obtained with the FIG. 9 implementation.
Figure 11:
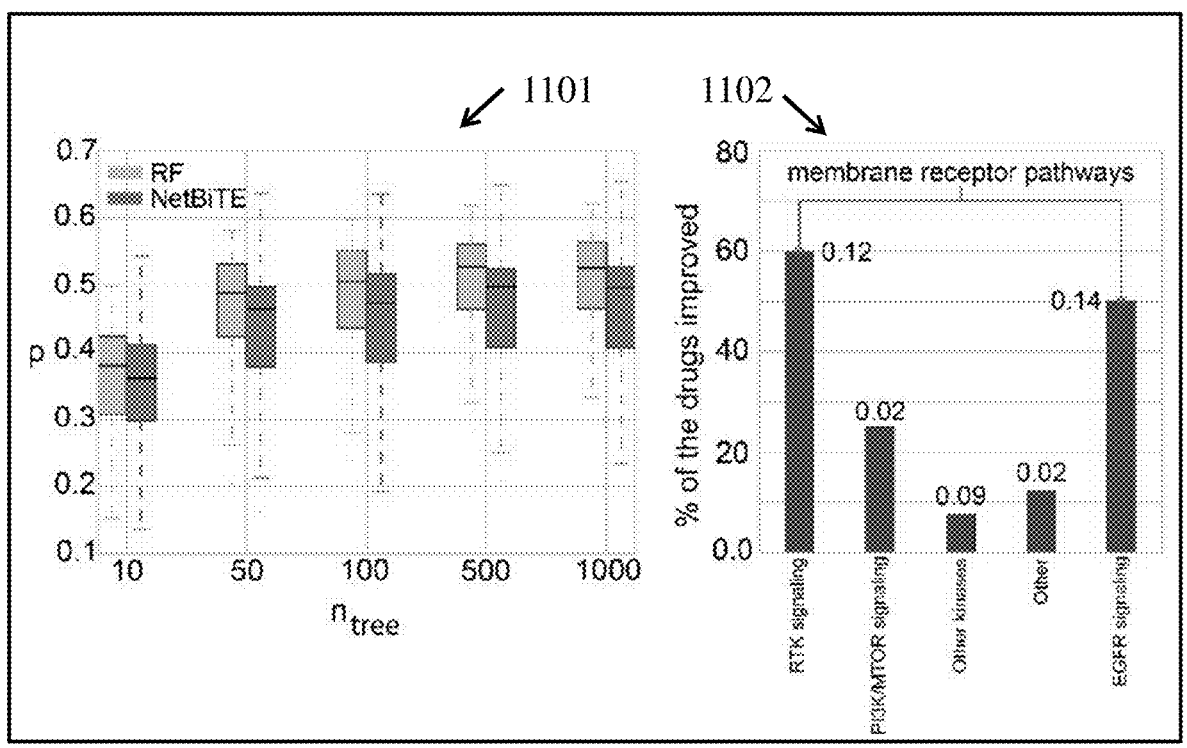

FIG. 10 shows a histogram for the drug categories within the panel of 50 drugs studied. FIG. 11 shows a comparison of the predictive performance of the NetBiTE and RF models. The rectangular blocks in the left-hand plot 1101 here indicate Pearson correlation of the predicted $IC_{50}$ and true $IC_{50}$ for the set of 50 drugs for NetBiTE (dark grey) and RF (light grey), and the dashed vertical lines indicate the range of results in each case. While at first glance the NetBiTE results do not appear more accurate than RF for this particular application, closer inspection reveals a high variation in accuracy gain across the different drug categories. In particular, the histogram on the right plot 1102 of the figure demonstrates significant improvement in prediction accuracy with NetBiTE for drugs that target membrane receptor pathways. NetBiTE $IC_{50}$ predictions for RTK (receptor tyrosine kinase) and EGFR (epidermal growth factor receptor) signaling pathway inhibitors experience the most frequent (60% and 50% of the drugs respectively) and significant improvements in accuracy, with RTK inhibitors exhibiting a 25% improvement ($\Delta\rho=0.12$) and EGFR inhibitors a 30% improvement ($\Delta\rho=0.14$). These results suggest that, for drugs targeting membrane receptor pathways, the expression of their target genes are informative biomarkers for $IC_{50}$ drug sensitivity, while this is not the case for targets reported in the literature for other categories of cancer drugs studied here.

Figure 12:
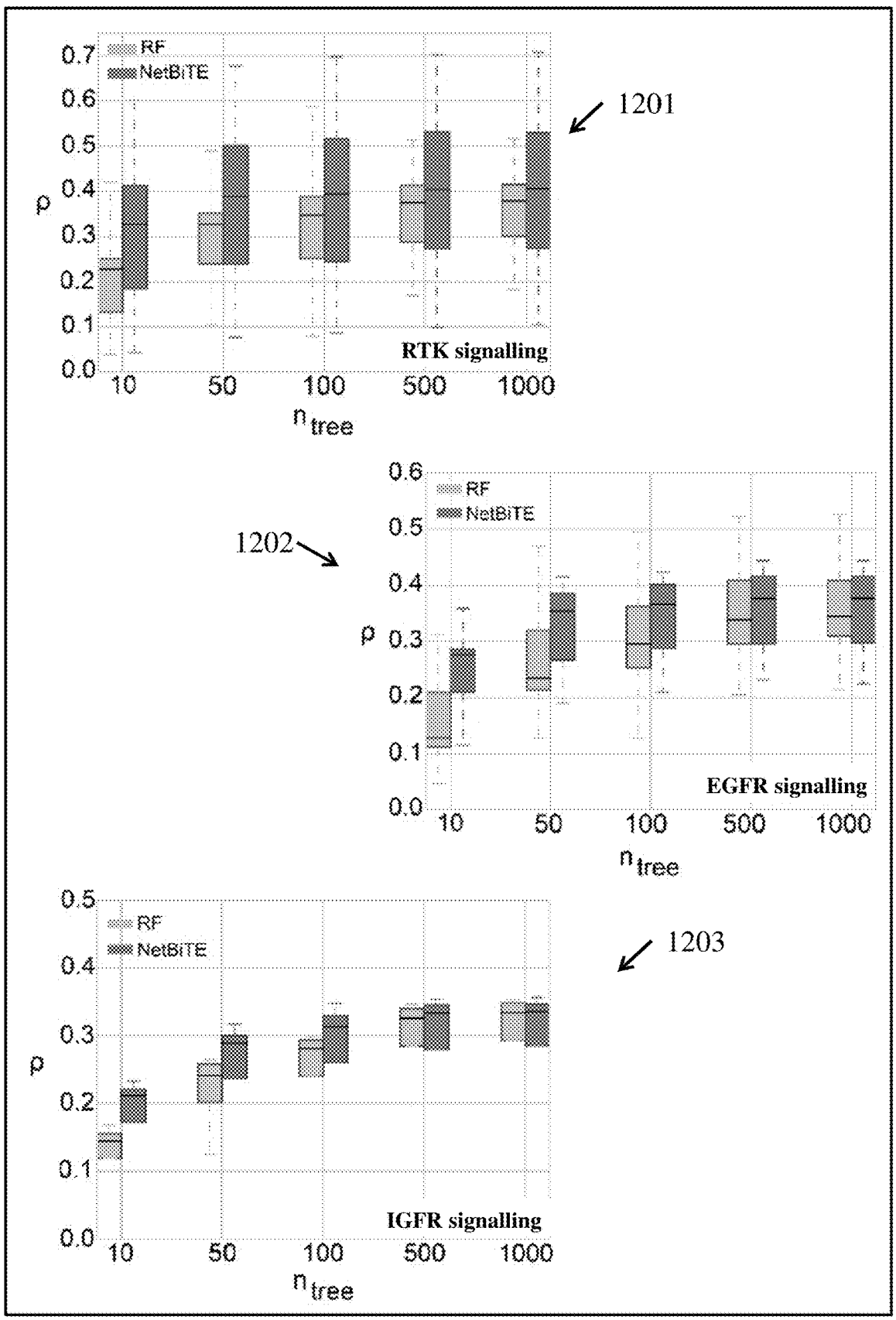

Results obtained by applying the NetBiTE and RF methods to all membrane receptor pathways inhibitors (MRPIs) within the GDSC database are shown in FIG. 12. These drugs were inhibitors of three pathways: RTK signaling (21 drugs), EGFR signaling (7 drugs) and IGFR (insulin-like growth factor 1 receptor) signaling (4 drugs). For RTK signaling pathway inhibitors (upper plot 1201), NetBiTE is superior to RF particularly at lower tree numbers, and 70% of these drugs showed improvement with NetBiTE for all numbers of trees. The central plot 1202 and lower plot 1203 show similar results for EGFR and IGFR signaling pathway inhibitors respectively, demonstrating accuracy improvement with NetBiTE that is especially significant at lower tree numbers.

It will be seen from the above that embodiments provide highly efficient model generation methods for drug efficacy prediction. Accurate models can be generated with significantly lower computational cost, and improved accuracy can be achieved for personalized drug efficacy prediction. Methods herein can be integrated in processes for treatment of patients by medical personnel. Such a process may include making gene expression measurements for a patient to obtain gene expression data, and performing a computer-implemented method as described above, using the patient's gene expression data, to obtain a personalized drug efficacy prediction for that patient. The process may include treating the patient in dependence on the drug efficacy prediction, e.g. by selecting appropriate medication(s) and/or dosages for a personalized treatment plan.

It will be appreciated that various changes and modifications can be made to the exemplary embodiments described. For example, methods embodying exemplary embodiments of the invention may of course be applied to genetic diseases other than cancer. By way of example, other multifactorial genetic diseases displaying different subtypes caused by different genetic mutations include cardiovascular disease and Alzheimer disease.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, the method comprising:
   determining relevance of a gene to efficacy of a particular pharmaceutical drug based on prior knowledge indicating known or predicted sensitivity of genetic characteristics to action of the particular pharmaceutical drug;
   storing, based on a dataset correlating data for disease-cell samples with drug efficacy values for the disease-cell samples, bias weights corresponding to respective genes in samples, the bias weights being dependent on relevance of respective genes to drug efficacy for the respective genes and being determined prior to generating a machine learning model, wherein bias weights assigned to genes relevant to drug efficacy are assigned higher values than what are assigned as values for bias weights assigned to genes that are non-relevant to drug efficacy;
   generating the machine learning model for drug efficacy prediction in treatment of genetic disease from the dataset, the generating the machine learning model comprising:
     processing said dataset via a tree ensemble method wherein decision trees are grown with splits corresponding to respective genes in said samples, the genes for the splits being chosen from respective subsets of said genes and based on respective selection probabilities dependent on corresponding bias weights and the bias weights are translated during the processing into the selection probabilities for generating the splits; and
     storing said machine learning model for prediction of drug efficacy values based on gene expression data of patients.

2. The method as claimed in claim 1, including, prior to generating the machine learning model, propagating said bias weights over a predetermined network indicating interaction between said genes to obtain respective smoothed bias weights, wherein said selection probabilities are dependent on the smoothed bias weights.

3. The method as claimed in claim 2, wherein said predetermined network comprises a protein-protein interaction network.

4. The method as claimed in claim 2, further comprising, after storing said machine learning model:
   receiving gene expression data of a patient;
   applying the machine learning model to that gene expression data to obtain a drug efficacy prediction for that patient; and
   outputting the drug efficacy prediction for use in treatment of the patient.

5. The method as claimed in claim 1, including storing said bias weights for each of a plurality of drugs, wherein said machine learning model comprises, for each of said drugs, a sub-model generated by the processing said dataset via said tree-ensemble method in which said selection probabilities are dependent on the bias weights for that drug and in which corresponding genes are selected for inclusion in splits formed in sub-models with respective probabilities that are dependent on the corresponding bias weights.

6. The method as claimed in claim 5, including, prior to generating the machine learning model, propagating said bias weights for each drug over a predetermined network indicating interaction between said genes to obtain respective smoothed bias weights for that drug, wherein said selection probabilities for generation of said sub-model for each drug are dependent on the smoothed bias weights for that drug.

7. The method as claimed in claim 5, wherein, for each of said drugs, each bias weight used to select a gene for inclusion in a split comprises one of a higher value dependent on predetermined relevance of the corresponding gene to efficacy of that drug or a lower value dependent on non-relevance respectively of the corresponding gene to efficacy of that drug.

8. The method as claimed in claim 6, further comprising, after storing said machine learning model:
receiving gene expression data of a patient;
applying the machine learning model to that gene expression data to obtain a drug efficacy prediction for that patient; and
outputting the drug efficacy prediction for use in treatment of the patient.

9. The method as claimed in claim 1, wherein said disease-cell samples comprise cancer-cell samples and said machine learning model is generated for at least one membrane receptor pathway inhibitor drug.

10. A computing system, comprising one or more processors and a memory having program instructions thereon, wherein the one or more processors, in response to retrieval and execution of the program instructions cause the computing system to:
determine relevance of a gene to efficacy of a particular pharmaceutical drug based on prior knowledge indicating known or predicted sensitivity of genetic characteristics to action of the particular pharmaceutical drug;
store, based on a dataset correlating data for disease-cell samples with drug efficacy values for the disease-cell samples, bias weights corresponding to respective genes in samples, the bias weights being dependent on relevance of respective genes to drug efficacy for the respective genes and being determined prior to generating a machine learning model, wherein bias weights assigned to genes relevant to drug efficacy are assigned higher values than what are assigned as values for bias weights assigned to genes that are non-relevant to drug efficacy;
generate the machine learning model for drug efficacy prediction in treatment of genetic disease from the dataset, the generating the machine learning model comprising:
process said dataset via a tree ensemble method wherein decision trees are grown with splits corresponding to respective genes in said samples, the genes for the splits being chosen from respective subsets of said genes and based on respective selection probabilities dependent on corresponding bias weights and the bias weights are translated during the processing into the selection probabilities for generating the splits; and
store said machine learning model for prediction of drug efficacy values based on gene expression data of patients.

11. The computing system as claimed in claim 10, said program instructions being further executable to cause the computing system, prior to generating the machine learning model, to propagate said bias weights over a predetermined network indicating interaction between said genes to obtain respective smoothed bias weights, wherein said selection probabilities are dependent on the smoothed bias weights.

12. The computing system as claimed in claim 11, said program instructions being further executable to cause the computing system, in response to receipt of gene expression data of a patient after storing said machine learning model, to apply the machine learning model to that gene expression data to obtain a drug efficacy prediction for that patient, and to output the drug efficacy prediction for use in treatment of the patient.

13. The computing system as claimed in claim 10, said program instructions being executable to cause the computing system to store said bias weights for each of a plurality of drugs, and to generate said machine learning model such that the machine learning model comprises, for each of said drugs, a sub-model generated by the processing said dataset via said tree-ensemble method in which said selection probabilities are dependent on the bias weights for that drug and in which corresponding genes are selected for inclusion in splits foiined in sub-models with respective probabilities that are dependent on the corresponding bias weights.

14. The computing system as claimed in claim 13, said program instructions being further executable to cause the computing system, prior to generating the machine learning model, to propagate said bias weights for each drug over a predetermined network indicating interaction between said genes to obtain respective smoothed bias weights for that drug, wherein said selection probabilities for generation of said sub-model for each drug are dependent on the smoothed bias weights for that drug.

15. The computing system as claimed in claim 14, said program instructions being further executable to cause the computing system, in response to receipt of gene expression data of a patient after storing said machine learning model, to apply the machine learning model to that gene expression data to obtain a drug efficacy prediction for that patient, and to output the drug efficacy prediction for use in treatment of the patient.

16. A drug efficacy prediction method, the method comprising:
treating a genetic disease of a patient, at least by making gene expression measurements for the patient to obtain gene expression data, and by performing the following computer-implemented method to obtain a drug efficacy prediction for that patient:
determining relevance of a gene to efficacy of a particular pharmaceutical drug based on prior knowledge indicating known or predicted sensitivity of genetic characteristics to action of the particular pharmaceutical drug;
storing, based on a dataset correlating data for disease-cell samples with drug efficacy values for the disease-cell samples, bias weights corresponding to respective genes in samples, the bias weights being dependent on relevance of respective genes to drug efficacy for the respective genes and being determined prior to generating a machine learning model, wherein bias weights assigned to genes relevant to drug efficacy are assigned higher values than what are assigned as values for bias weights assigned to genes that are non-relevant to drug efficacy;

generating the machine learning model for drug efficacy prediction in treatment of genetic disease from the dataset, the generating the machine learning model comprising:

processing said dataset via a tree ensemble method wherein decision trees are grown with splits corresponding to respective genes in said samples, the genes for the splits being chosen from respective subsets of said genes and based on respective selection probabilities dependent on corresponding bias weights and the bias weights are translated during the processing into the selection probabilities for generating the splits; and storing said machine learning model;

receiving gene expression data of the patient;

applying the machine learning model to that gene expression data to obtain a drug efficacy prediction for the patient; and outputting the drug efficacy prediction for use in treatment of the patient.

17. The method as claimed in claim 16 including treating the patient in dependence on said drug efficacy prediction.

18. The method as claimed in claim 16, wherein said drug efficacy prediction method includes:

storing said bias weights for each of a plurality of drugs, and said machine learning model comprises, for each of said drugs, a sub-model generated by the processing said dataset via said tree-ensemble method in which said selection probabilities are dependent on the bias weights for that drug; and prior to generating the machine learning model, propagating said bias weights for each drug over a predetermined network indicating interaction between said genes to obtain respective smoothed bias weights for that drug, wherein said selection probabilities for generation of said sub-model for each drug are dependent on the smoothed bias weights for that drug.

19. The method as claimed in claim 18 including treating the patient in dependence on said drug efficacy prediction.

* * * * *